United States Patent
Huemer

(10) Patent No.: US 9,835,531 B2
(45) Date of Patent: Dec. 5, 2017

(54) METHOD AND SEPARATION DEVICE FOR SEPARATING A FILTRATE FROM A SAMPLE FLUID

(71) Applicant: Roche Diagnostics Operations, Inc., Indianapolis, IN (US)

(72) Inventor: Herfried Huemer, Feldbach (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 250 days.

(21) Appl. No.: 14/615,700

(22) Filed: Feb. 6, 2015

(65) Prior Publication Data
US 2015/0153258 A1   Jun. 4, 2015

Related U.S. Application Data

(63) Continuation of application No. PCT/EP2013/066550, filed on Aug. 7, 2013.

(30) Foreign Application Priority Data

Aug. 9, 2012   (EP) ..................................... 12179912

(51) Int. Cl.
   *G01N 1/40*   (2006.01)
   *G01N 33/49*   (2006.01)
   (Continued)

(52) U.S. Cl.
   CPC ............ *G01N 1/4077* (2013.01); *B01D 24/30* (2013.01); *B01D 63/08* (2013.01); *B01L 3/5021* (2013.01);
   (Continued)

(58) Field of Classification Search
   CPC ............ B01D 2313/24; B01D 2313/50; B01D 2313/05; B01D 24/30; B01D 63/08;
   (Continued)

(56) References Cited

U.S. PATENT DOCUMENTS

| 3,814,079 A | 6/1974 | Le Roy, Sr. |
| 4,021,352 A | 5/1977 | Sarstedt |

(Continued)

FOREIGN PATENT DOCUMENTS

| CN | 101909757 A | 12/2010 |
| EP | 0292329 A2 | 11/1988 |

(Continued)

OTHER PUBLICATIONS

International Search Report dated Mar. 5, 2014 in Application No. PCT/EP2013/066550, 5 pages.

*Primary Examiner* — John Kim
(74) *Attorney, Agent, or Firm* — Roche Diagnostics Operations, Inc.

(57) ABSTRACT

A separation device for separating a filtrate from a sample fluid, especially for extracting plasma from whole blood, comprising a sample container for receiving the sample fluid and a filter plunger to be introduced under seal into the sample container, which filter plunger has a filter element at its front end and a grip element on the opposite end and will receive in its interior the filtrate obtained. After insertion of the filter plunger into the sample container an annular chamber is formed between the inner wall of the sample container and the outer wall of the filter plunger, which is sealed against the exterior by a sealing lip and in which an air cushion is formed upon introduction of the filter plunger into the sample container, which acts on the sample fluid. A flow connection is provided between the annular chamber and the front side of the filter element after insertion of the filter plunger is terminated.

16 Claims, 4 Drawing Sheets

(51) Int. Cl.
  *B01D 63/08* (2006.01)
  *B01D 24/30* (2006.01)
  *B01L 3/00* (2006.01)
(52) U.S. Cl.
  CPC ....... *G01N 33/491* (2013.01); *B01D 2313/24* (2013.01); *B01D 2313/50* (2013.01); *B01D 2315/05* (2013.01); *B01L 2300/047* (2013.01); *B01L 2300/0681* (2013.01); *B01L 2400/0478* (2013.01); *G01N 2001/4088* (2013.01)
(58) Field of Classification Search
  CPC ....... B01L 2300/047; B01L 2300/0681; B01L 2400/0478; B01L 3/5021; G01N 1/4077; G01N 2001/4088; G01N 33/491
  See application file for complete search history.

(56) References Cited

U.S. PATENT DOCUMENTS

| | | |
|---|---|---|
| 4,046,145 A | 9/1977 | Choksi et al. |
| 4,131,549 A | 12/1978 | Ferrara |
| 4,891,134 A | 1/1990 | Vcelka |
| 4,921,618 A * | 5/1990 | Hamlin ............. B01D 17/0214 210/780 |
| 4,962,044 A | 10/1990 | Knesel, Jr. et al. |
| 4,990,253 A | 2/1991 | Vcelka |
| 5,074,312 A | 12/1991 | Sarstedt |
| 5,234,608 A | 8/1993 | Duff |
| 5,262,067 A | 11/1993 | Wilk et al. |
| 5,336,412 A | 8/1994 | Huse et al. |
| 5,364,533 A | 11/1994 | Ogura et al. |
| 5,549,816 A | 8/1996 | Harp et al. |
| 5,578,459 A | 11/1996 | Gordon et al. |
| 5,637,087 A | 6/1997 | O'Neil et al. |
| 5,672,481 A | 9/1997 | Minshall et al. |
| 5,919,356 A | 7/1999 | Hood |
| 6,039,868 A | 3/2000 | Allen et al. |
| 6,117,394 A | 9/2000 | Smith |
| 6,241,947 B1 | 6/2001 | Komatsu et al. |
| 6,669,905 B1 | 12/2003 | Mathias et al. |
| 6,761,855 B1 | 7/2004 | Cook et al. |
| 2002/0134175 A1 | 9/2002 | Mehra et al. |
| 2002/0143298 A1 | 10/2002 | Marsden |
| 2008/0015470 A1 | 1/2008 | Sarstedt |
| 2010/0093551 A1 | 4/2010 | Montagu |
| 2012/0118825 A1 | 5/2012 | Margraf et al. |
| 2012/0160331 A1 | 6/2012 | Egger-Clmenti et al. |

FOREIGN PATENT DOCUMENTS

| | | |
|---|---|---|
| EP | 0297441 A2 | 1/1989 |
| EP | 0550950 A2 | 7/1993 |
| EP | 0932042 A2 | 7/1999 |
| EP | 1469068 A1 | 10/2004 |
| JP | H05-95721 A | 4/1993 |
| JP | 2002-277357 A | 9/2002 |
| WO | 94/25848 A1 | 11/1994 |
| WO | 1996/024425 A1 | 8/1996 |
| WO | 2011/033000 A2 | 3/2011 |
| WO | 2012/062651 A1 | 5/2012 |

* cited by examiner

METHOD AND SEPARATION DEVICE FOR SEPARATING A FILTRATE FROM A SAMPLE FLUID

CROSS-REFERENCE TO RELATED APPLICATIONS

This application is a continuation of International Patent Application No. PCT/EP2013/066550, filed 7 Aug. 2013, which claims the benefit of European Patent Application No. 12179912.6 filed 9 Aug. 2012, the disclosures of which are hereby incorporated herein by reference in their entirety.

BACKGROUND

The present disclosure relates to a method and to a separation device for separating a filtrate from a sample fluid, in particular for extracting plasma from whole blood.

Besides centrifuges, which are used mainly in laboratories for separating plasma from whole blood, there have become known a number of devices for obtaining very small amounts of plasma at Point of Care (PoC) settings by separating plasma from whole blood by means of filtering.

In the simplest case plasma separation may be effected by means of a multilayer test strip as described in U.S. Pat. No. 5,262,067 A (BOEHRINGER MANNHEIM), where a transport layer on an inert carrier layer is provided for transporting sample fluid (whole blood) from an input area to a measuring area. The transport layer may for instance be made of glass fibre mat, which in the input area is covered by a plasma separation layer. The procedure is however only suitable for analysers which process test strips.

From WHATMAN INC. Florham Park, N.J. 07932, USA, there is known a separation device under the name of "Mini-UniPrep", which is suitable for preparing samples for High Performance Liquid Chromatography (HPLC). The unfiltered sample is filled into a sample container and then a filtration plunger is introduced, which has a filter at its front end. The filtration plunger is pushed into the sample container until the separated filtrate fills its interior while the replaced air is vented through a venting opening. The separation device may thereafter be directly inserted into the sample changer unit of an analyser. Withdrawal of the filtrate may be carried out via a septum in the cap of the filtration plunger. It is a disadvantage of this known separation device that the pressure exerted on the filter in the filtration plunger cannot be applied in an reproducible and uniform manner and that pressure peaks that are detrimental to the sample cannot be avoided. This is particularly harmful if the device is used for separating plasma from whole blood since pressure peaks may cause bursting of red blood cells (RBCs) (haemolysis), leading to undesirable contamination of the plasma fraction by the released content substances of the RBCs.

From U.S. Pat. No. 4,990,253 A, especially from FIGS. 4 to 6, a fluid sampling filtration device is known. An outer container of the device filled with a sample to be filtered slidably receives a hollow plunger having filter media disposed near a front end and sealing means disposed in an annular groove about the periphery of the plunger. In use, a liquid sample to be filtered is placed in the outer container. The plunger is inserted filter end first into the open end of the outer container and the sealing means sealingly engages the inner wall to form an air-tight seal between the outer container and the plunger. As the plunger is depressed further into the outer container, air is forced through the filter media and escapes through the loosely fitting cap. Once the plunger reaches the surface of the sample fluid to be filtered, a fixed quantity of air is trapped between the sealing means (O-ring) and the fluid level and, upon further depression of the plunger this trapped air is compressed. The pressurized air in turn forces the fluid sample through the filter media and into a collecting chamber in the interior of the hollow plunger. Filtration is complete when the plunger hits the bottom end of the outer container. Simultaneously, the O-ring snaps past nubs formed in the inner wall of container to lock the two components together. It is a disadvantage of this known filtration that the filtration is terminated after the plunger contacts the bottom of the outer container.

EP 0 297 441 A2 discloses a separation and transfer device comprising a container tube for holding a desired quantity of a liquid and an open-ended, tubular plunger having an O-ring for forming a liquid-tight seal with the interior of the container tube, wherein the seal is maintained while the plunger slides within the tube. The device further comprises a liquid collection cup which is positioned below the plunger while the plunger is depressed. The collection cup and the plunger are furnished with means for allowing the passage of displaced gas during the depression of the plunger. The separation is completed when the plunger hits the bottom of the container tube. There are the same disadvantages as stated above.

It is an object of the present disclosure to propose improvements of the separation device as described above (e.g., "Mini-UniPrep" by WHATMAN INC. or U.S. Pat. No. 4,990,253 A), which will permit the reproducible extraction of plasma samples from relatively small whole blood samples whilst providing easy handling for the user.

SUMMARY

It is against the above background that the present disclosure provides certain unobvious advantages and advancements over the prior art. In particular, the inventors have recognized a need for improvements in plasma separation systems and methods for plasma separation. In accordance with an embodiment of the disclosure, a separation device for separating a filtrate from a sample fluid, in particular for extracting plasma from whole blood, is provided comprising a sample container for receiving the sample fluid and a filter plunger to be introduced under seal into the sample container, which filter plunger has a filter element at its front end and a grip element on the opposite end, and will receive in its interior the filtrate obtained This object is achieved by the embodiments of the disclosure by proposing that the annular chamber is flow-connected with the front side of the filter element after insertion of the filter plunger is terminated. In contrast to the state of the art pressure will be applied on the sample fluid, e.g., a whole blood sample, not in a direct uncontrolled way, but slowly and uniformly decreasing via the compressed air cushion, with the pressure situation being defined and adjustable by the geometric dimensions (for instance the volume ratios) of the individual parts of the separation device and the characteristics of the filter element.

The rim of the filter plunger extends beyond the front face of filter element (i.e., the side in contact with the sample fluid) and forms a frontal wetting chamber. In this chamber there are provided recesses in the rim or flow openings that establish flow connection between the annular chamber and the frontal wetting chamber. These flow openings on the lower rim of the filter plunger permit inflow of the blood sample after the filter plunger has already been pushed fully to the bottom of the sample container.

Alternatively or additionally, the bottom of the sample container may have notches or groove-shaped recesses for establishing flow connection between the annular chamber and the front side of the filter element, after the sample-side rim is in contact with the bottom of the sample container.

The method according to the disclosure for separating filtrate from a sample fluid, especially for extracting plasma from whole blood, is characterized by the following steps:

Providing a sample container with sample fluid;

Inserting a filter plunger into the sample container until it meets the bottom of the sample container establishing a pressurized air cushion—acting on the sample fluid—in an annular chamber between filter plunger and sample container closed by a sealing element against the outside (ambient air);

Pressing the sample fluid through a filter element disposed in the filter plunger by means of the excess pressure in the annular chamber, using a flow connection between the annular chamber and the front side of the filter element, and causing the filtrate to exit on the output side of the filter element; and Collecting the filtrate in a filtrate collector vessel contained in the filter plunger.

In accordance with one or more embodiments of the disclosure, the collector vessel containing whole blood can be connected to a filter unit by introducing a suction tube and an aeration tube of the filter unit into the collector vessel. Also, the partial vacuum in the filtering device can be controlled by a control device of the analyser, typically by pressure dependent control of the flow rate of the suction pump.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

Figure 1:
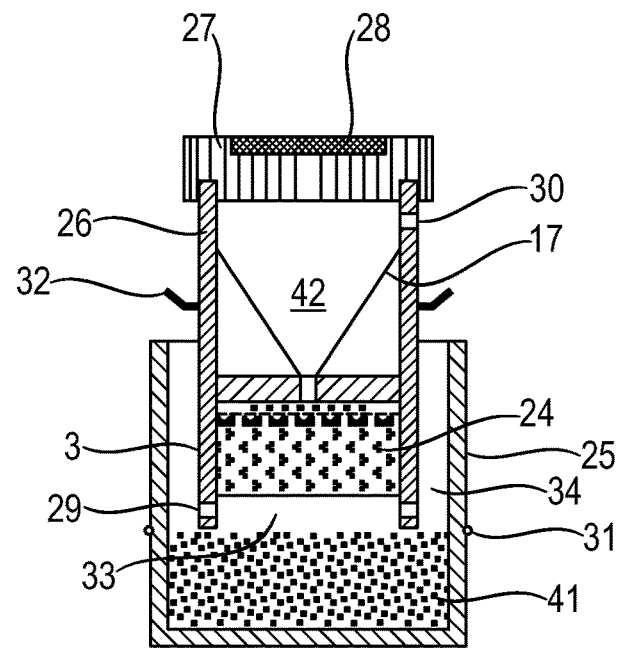
FIG. 1 is a separation device according to the disclosure for separating a filtrate from a sample fluid in a sectional view.
Figure 2:
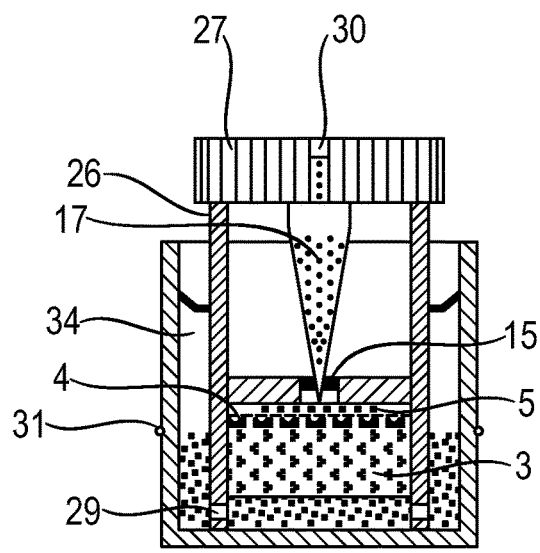
FIG. 2 is an alternative variant of the separation device of the disclosure.

The separation device shown in FIGS. 1 and 2 essentially comprises a sample container 25 (for instance a cylindrical sample cuvette) into which, after having been filled with whole blood 41 up to a mark 31, a filter plunger 26 is inserted, which contains a filter element 24 on the side facing the sample. In a space of the filter plunger 26 closed by the grip element 27 there is disposed a conical filtrate collector vessel 17 for the separated plasma 42, which is connected to the output side of the filter element 24. Between the inner wall of the sample container 25 and the outer wall of the filter plunger 26 there is formed an annular chamber 34 closed against the outside by as sealing element 32, typically a sealing lip, in which chamber 34 there is generated an air cushion acting on the sample fluid when the filter plunger 26 is introduced. The sealing element or sealing lip 32 may be formed onto the outer wall of the filter plunger 26 or may be an integral part of the outer wall of the filter plunger 26 in the form of a sealing shoulder.

In accordance with another embodiment of the disclosure, additional fixating elements are optionally provided, for instance snap-on connectors or the like, between the sample container 25 and the filter plunger 26, which permit locking the filter plunger 26 in the depressed position and thus prevent it from being pushed upwards again by the built-up pressure, which would diminish the pressure of the air cushion established. If there is enough friction between the sealing lip 32 and the wall of the sample container 25, however, this may suffice to make the filter plunger remain in its depressed position even without additional fixating elements.

On the side of the sample the rim of the filter plunger 26 extends beyond the filter element 24 and forms a frontal wetting chamber 33, in which recesses in the rim or flow openings 29 provide a flow connection from the annular chamber 34 into the frontal wetting chamber 33. The filter plunger 26 is vented via an opening 30 in the area of the grip element 27.

Figure 8:
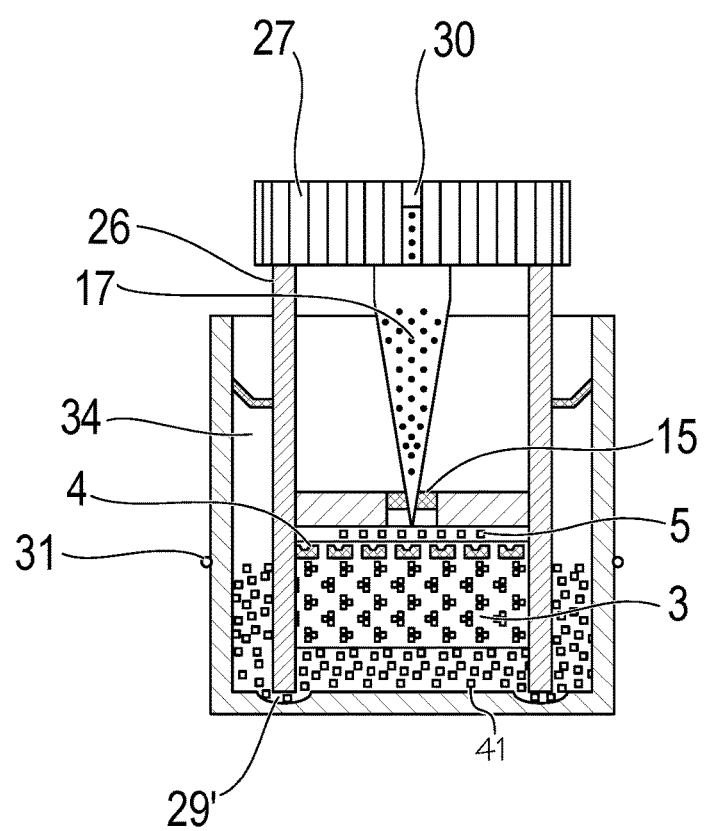
FIG. 8 is a separation device according to another embodiment of the disclosure, wherein the bottom of the sample container has notches or groove-shaped recesses formed therein.
Figure 9:
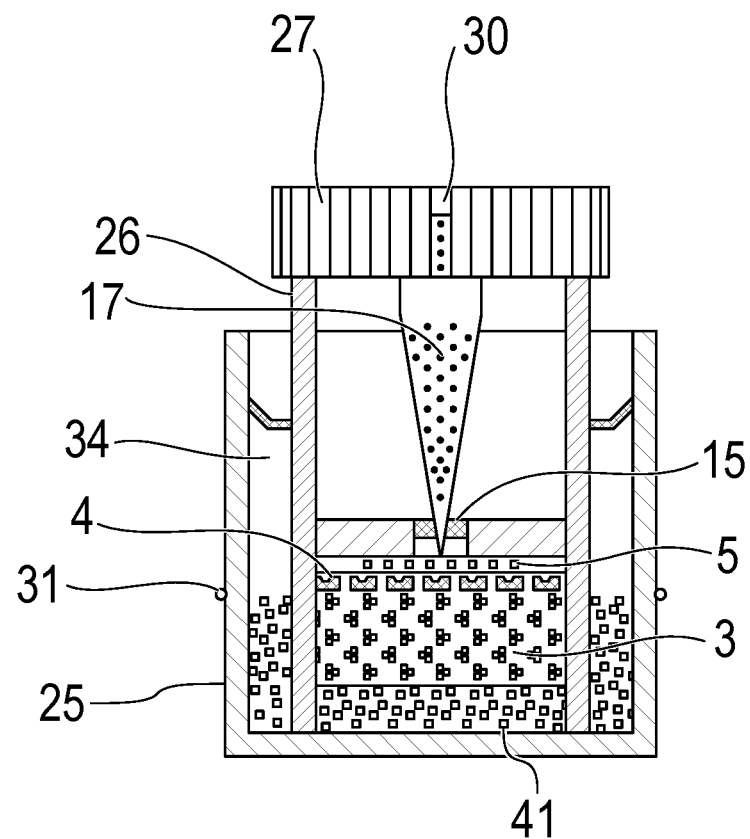
FIG. 9 is an alternative cross-sectional view of the embodiment shown in FIG. 8, wherein the sample-side rim of the filter plunger is in contact with the bottom of the sample container.

Alternatively, notches or groove-shaped recesses 29' may be provided in the bottom of the sample container 25 (FIG. 8), which establish a flow connection from the annular chamber 34 to the front side of the filter element 24 or to the wetting chamber 33.

In the variant of FIG. 1, the grip element 27 of the filter plunger 26 has a puncturable membrane 28 for withdrawing filtrate from the filtrate collector vessel 17.

According to the variant shown in FIG. 2, the filtrate collector vessel 17 is attached to the grip element 27 of the filter plunger 26, and the grip element 27 together with filtrate collector vessel 17 may be unscrewed or wrenched off the filter plunger, such that the conical pointed filtrate collector vessel 17 (Plasma Tip) may be directly docked onto the input element of an analyser. A venting channel 30 may be provided in the grip element 27 typically covered by a gas-permeable membrane.

The filter element 24 of the filter plunger 26 is for instance configured as a layered filter consisting of a deep-bed filter 3, a stop membrane 4 and a lateral grid 5.

Figure 3:
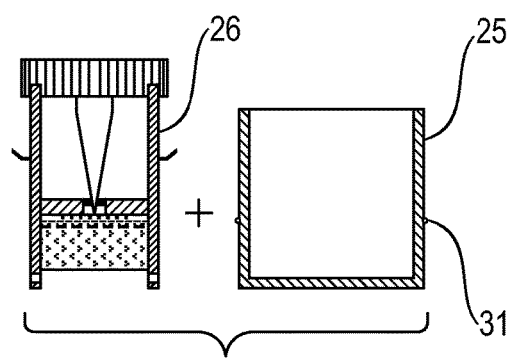
FIGS. 3 to 7 illustrate the use of the separation device of the embodiment of the disclosure presented in FIG. 2, in a series of procedure steps following one after the other.

Plasma extraction by means of the separation device of the embodiment of the disclosure according to FIG. 2 may be carried out in the following way:

Taking the separation device comprising sample container 25 and filter plunger 26 from a sterile package and detaching the filter plunger 26 from the sample container 25 (FIG. 3).

Figure 4:
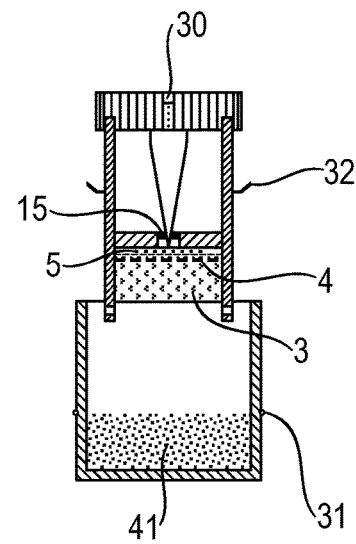

Filling the sample container 25 with whole blood 41 up to the mark 31, (for instance 500 μl, typically 1 ml) for instance using a syringe or a pipetting device, and putting in place the filter plunger 26 with sealing element 32 (FIG. 4).

Pushing the filter plunger 26 down until it meets the bottom of the sample container 25 by pressing on the grip element 27.

Due to the downward movement of the filter plunger 26 and the developing airtight seal between the sealing lip 32 on the outside of the filter plunger 26 and the inner wall of the sample container 25, an air cushion is formed between the sealing lip 32 and the surface of the blood sample 41 present in the annular chamber 34. As the filter plunger 26 progresses excess pressure is built up in the annular chamber 34.

Figure 5:
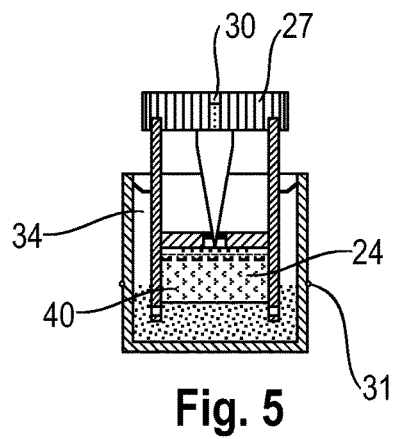

On account of the downward movement of the filter plunger 26 the front side of the filter element 24 in the frontal wetting chamber 33 thus formed is wetted by the blood sample 41 and at the same time excess pressure is built up in the annular chamber 34 between the outer wall of the plunger 26 and the inner wall of the sample container 25 (FIG. 5).

The flow openings 29 on the lower rim of the filter plunger 26 permit further inflow of the blood sample 41. The venting passage 30 or, if present, the air-permeable covering membrane 28 permit the plasma level in the filtrate collector vessel 17 to rise.

The deep-bed filter 3 of the filter element 24 may for instance be built up from glass fibers without binding agent (typically FV-2, Whatman Inc, resp. DE 40 15 589 A1, or EP 0 239 002 A1, Böhringer-Mannheim) with a retention range of 0.5 μm to 10 μm, typically 1 μm to 5 μm, more typically <3 μm. The red blood cells (RBCs) will collect on the thin glass fibers of the deep-bed filter 3 without bursting or unduly influencing the rate of flow.

Figure 6:
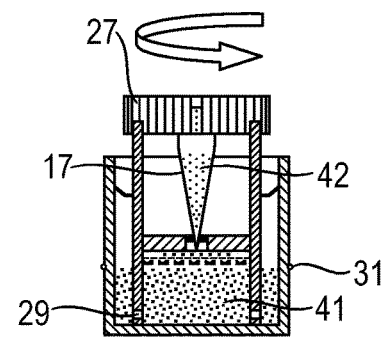

Depending on the cross-section of the filter element 24 in the filter plunger 26 and on haematocrit a "plasma front" or "plasma fraction" 40 will form, which can pass the stop membrane 4 unimpededly. Residual RBCs not held back by the deep-bed filter are filtered out by the stop membrane 4 (FIG. 6). For this purpose the stop membrane 4 has a pore size significantly smaller than that of the deep-bed filter 3, i.e., pore diameters of less than 400 nm, typically less than 200 nm. By combining a deep-bed filter 3, which on account of its pore size already retains the greater part of blood cells but does not impede the flow of the plasma fraction, with a subsequent stop membrane 4, which due to its smaller pore size will reliably retain remaining blood cells but would clog swiftly if the preceding deep-bed filter 3 were absent, on account of its limited number of pores, a reliable separation of blood cells without clogging of the filter can be achieved, thus making it possible to obtain a sufficiently large volume of plasma sample.

The excess pressure of not more than 500 mbar, typically 300 mbar, more typically 100 mbar to 150 mbar, which is established depending on the filter characteristics and the geometry of the wetting chamber 33 and the annular chamber 34, will determine the flow rate and thus the shear forces acting especially on the RBCs within the stop membrane 4. Bursting of RBCs (haemolysis) can efficiently be prevented by optimizing the pressure volume in the annular chamber 34.

The lateral grid 5 of the filter element 24 permits plasma 42 to be collected and sucked off behind the stop membrane 4 towards the filtrate collector vessel 17, and prevents the stop membrane 4 from "sealing off" tightly. Due to its grid structure the lateral grid 5 acts as a non-continuous support for the stop membrane 4, letting plasma flow out on the output side of the stop membrane 4 into the filtrate collector vessel 17. By forming channels the grid structure furthermore enables plasma which exits over the area of the stop membrane 4, to converge towards the area of the filtrate collector vessel 17 and to flow into it.

(Alternatively, this functionality of the lateral grid 5 may also be provided by stamping the bottom of the filter plunger 26 on the output side or otherwise providing for sufficient roughness of its surface.)

Plasma extraction will generally end when the plasma front 40 reaches the stop membrane 4.

In the case of haematocrit <40% plasma extraction may come to a halt due to premature pressure compensation. (Alternatively, plasma extraction may for instance also be stopped if the filtrate collector vessel 17 has a venting opening closed by a hydrophobic membrane, which upon complete filling of the filtrate collector vessel will prevent further inflow of filtrate, thus ending plasma extraction).

By means of the marks on the filtrate collector vessel 17 visual inspection can determine whether the desired amount of plasma has been obtained.

Removing the filtrate collector vessel 17 by a turn of the grip element 27 (FIG. 6, 7).

(Alternatively: plasma may be taken out through a perforated covering membrane 28 (FIG. 1)).

(Alternatively: the tip of the filtrate collector vessel 17 may be configured as a Luer cone).

Figure 7:
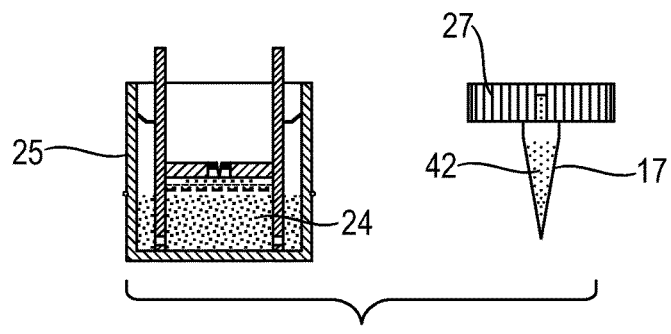

The sample container 25 with the remaining pieces of the filter plunger serves as a waste receptacle and may be discarded in a contamination-free way (FIG. 7).

It is noted that terms like "preferably", "commonly" and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these preferred aspects.

What is claimed is:

1. A separation device for separating a filtrate from a sample fluid comprising:
   a sample container for receiving the sample fluid,
   a filter plunger to be introduced into the sample container, which filter plunger has a filter element at its front end, a grip element on an opposite end, and an interior to receive the filtrate obtained, wherein
   an annular chamber is formed between an inner wall of the sample container and an outer wall of the filter plunger after insertion of the filter plunger into the sample container, which annular chamber is sealed against the exterior by a sealing element and in which an air cushion, acting on the sample fluid, is formed upon introduction of the filter plunger into the sample container,
   the annular chamber is flow-connected with the front side of the filter element after a sample-side rim of the filter plunger is in contact with the bottom of the sample container and thus insertion of the filter plunger is terminated,
   a recess of the grip element of the filter plunger contains a filtrate collector vessel that contacts the filter element,
   the filtrate collector vessel is attached to the grip element of the filter plunger and the grip element together with the filtrate collector vessel is removable from the filter plunger, and
   the sample-side rim of the filter plunger extends beyond the front face of the filter element and forms a frontal wetting chamber in which are provided recesses in the rim or flow openings which establish flow connection between the annular chamber and the frontal wetting chamber.

2. The separation device according to claim 1, wherein the filtrate collector vessel tapers towards the filter element.

3. The separation device according to claim 1, wherein the grip element together with the filtrate collector vessel can be unscrewed from or wrenched off the filter plunger.

4. The separation device according to claim 1, wherein the grip element of the filter plunger is provided with a puncturable membrane for withdrawing filtrate from the filtrate collector vessel.

5. The separation device according to claim 1, wherein the filter element is a layered filter.

6. The separation device of claim 5, wherein the layered filter comprises a deep-bed filter, a stop membrane and a lateral grid.

7. The separation device according to claim 1, wherein the filtrate collector vessel has a tip that contacts the filter element.

8. The separation device according to claim 1, wherein the filtrate is plasma and the sample fluid is whole blood.

9. A separation device for separating a filtrate from a sample fluid comprising:
   a sample container for receiving the sample fluid,
   a filter plunger to be introduced into the sample container, which filter plunger has a filter element at its front end, a grip element on an opposite end, and an interior to receive the filtrate obtained, wherein
   an annular chamber is formed between an inner wall of the sample container and an outer wall of the filter plunger after insertion of the filter plunger into the sample container, which annular chamber is sealed against the exterior by a sealing element and in which an air cushion, acting on the sample fluid, is formed upon introduction of the filter plunger into the sample container,
   the annular chamber is flow-connected with the front side of the filter element after a sample-side rim of the filter plunger is in contact with the bottom of the sample container and thus insertion of the filter plunger is terminated,
   a recess of the grip element of the filter plunger contains a filtrate collector vessel that contacts the filter element,
   the filtrate collector vessel is attached to the grip element of the filter plunger and the grip element together with the filtrate collector vessel is removable from the filter plunger, and
   the bottom of the sample container has notches or groove-shaped recesses for establishing flow connection between the annular chamber and the front side of the filter element, after the sample-side rim is in contact with the bottom of the sample container.

10. The separation device according to claim 9, wherein the filtrate collector vessel tapers towards the filter element.

11. The separation device according to claim 9, wherein the filtrate collector vessel has a tip that contacts the filter element.

12. The separation device according to claim 9, wherein the grip element together with the filtrate collector vessel can be unscrewed from or wrenched off the filter plunger.

13. The separation device according to claim 9, wherein the grip element of the filter plunger is provided with a puncturable membrane for withdrawing filtrate from the filtrate collector vessel.

14. The separation device according to claim 9, wherein the filter element is a layered filter.

15. The separation device according to claim 14, wherein the layered filter comprises a deep-bed filter, a stop membrane and a lateral grid.

16. The separation device according to claim 9, wherein the filtrate is plasma and the sample fluid is whole blood.

* * * * *